United States Patent [19]

Iaccheri et al.

[11] Patent Number: 4,753,804

[45] Date of Patent: Jun. 28, 1988

[54] GRANULAR DIETETIC PRODUCT BASED ON AMINO ACIDS AND PROCESS FOR THEIR PREPARATION

[75] Inventors: Ennio Iaccheri, Burago Molgora; Tiziano Crimella; Giuseppe Ponti, both of Milan, all of Italy

[73] Assignee: Boehringer Biochemica S.p.A., Milan, Italy

[21] Appl. No.: 807,849

[22] Filed: Dec. 11, 1985

[30] Foreign Application Priority Data

Dec. 12, 1984 [IT] Italy .................................. 24003 A/84

[51] Int. Cl.[4] .......................... A61K 9/14; A61K 9/50; A61K 31/195

[52] U.S. Cl. .................................... 424/491; 424/489; 424/490; 424/493; 424/494; 424/496; 424/499; 514/561

[58] Field of Search ........................ 264/141, 142, 143; 426/516, 517; 514/561; 424/438, 482, 489, 490, 491, 493, 494, 496, 499

[56] References Cited

U.S. PATENT DOCUMENTS

| | | |
|---|---|---|
| 3,764,703 | 10/1973 | Bergström et al. ................ 424/319 |
| 3,773,930 | 11/1973 | Mohammed et al. ............... 424/257 |
| 3,956,611 | 4/1976 | Youngquist .......................... 426/93 |
| 4,001,441 | 1/1977 | Liepa .................................. 426/104 |
| 4,001,452 | 1/1977 | Williams ............................ 264/141 |
| 4,052,517 | 10/1977 | Youngquist ........................ 426/302 |
| 4,061,784 | 12/1977 | Youngquist .......................... 426/93 |
| 4,177,255 | 12/1979 | Dannelly ............................ 424/482 |
| 4,181,708 | 1/1980 | Dannelly ............................ 424/482 |
| 4,595,583 | 6/1986 | Eckenhoff et al. ................ 424/438 |
| 4,595,584 | 6/1986 | Wu et al. ............................ 424/438 |

FOREIGN PATENT DOCUMENTS 2037161 10/1973 United Kingdom .

Primary Examiner—Douglas W. Robinson
Attorney, Agent, or Firm—Browdy and Neimark

[57] ABSTRACT

Dietetic formulations for oral use are described, made up of compact pellets of mixtures of α-amino acids, possibly coated by a waterproof protective film, which may be disgregated in the gastrointestinal juices. The process for obtaining regular granules includes the coordinated extrusion and cutting of the powdery or pasty amino acid mixtures with the subsequent possible desiccation and coating by immersion in solutions of zein.

14 Claims, No Drawings

GRANULAR DIETETIC PRODUCT BASED ON AMINO ACIDS AND PROCESS FOR THEIR PREPARATION

FIELD OF THE INVENTION

The present invention concerns granular dietetic products and particularly high-density compact granules made up of mixture of L-α-aminoacids alone or in the presence of pharmacologically acceptable additives and excipients, as well as a process for their preparation.

DESCRIPTION OF THE PRIOR ART

As it is known, L-α-aminoacids form a class of compounds of vital importance for all the living organisms because they have an irreplaceable part in the metabolism and in its regulation.

Thus, under living conditions in which there is a great expense of energy, as on occasion of extended and repeated physical efforts as well as under situations of hypercatabolism, the requirement of amino acids, and particularly of the essential ones, is increased.

The same occurs under particular pathological situations, in which all the catabolic processes are raised, as e.g. in liver cirrhosis, hepatopathy and nephropathy of various origin, in the septic or cachectic states and in the morbid conditions which preceed or follow surgical operations. In many of these pathological situations, in which alterations in the aminoacid haematic values are noticed, administration of artificial mixtures of L-α-aminoacids in order to counter or to prevent the deficit has become a usual practice. For instance, in British Pat. No. 2037161 there is described a pharmaceutical preparation containing the essential branched chain aminoacids: leucine, isoleucine and valine in mutually different ratios, to be used in the treatment of hepatic encephalopathy by parenteral route and to be administered together with solutions of carbohydrates. The commonest formulations of this type are those providing administration of L-α-aminoacid mixtures by infusional route. The typology of these mixtures varies according to the pathological situations to be faced in the therapeutic practice. Thus, in the case of nephropatients, the loss of essential aminoacids "in toto" and particularly of the above mentioned branched chain aminoacids and of threonine is typical. From that there follows the therapeutical practice of administering to chronic uremic patients artificial mixtures of all the essential L-α-aminoacids, i.e.: threonine, lysine, tryptophan, phenylalanine, valine, leucine, isoleucine and histidine. The same type of nutritive integration is also suitable for the treatment of nephropatients who have to keep a hypoproteinic diet and in this case the contribution of aminoacids has the function of preventing the possible deficit ensuing from the hypoproteinic diet.

On the contrary, in pathologies such as liver cirrhosis the upset nitrogen balance is characterized by low haematic levels of urea and by hyperammoniaemia, while the levels of branched chain aminoacids, are lowered in a similar way. As branched chain aminoacids unlike the other aminoacids, go almost unchanged through liver and are principally metabolized in the muscular tissue, formulations have been proposed for hypodermic or infusional use, which are exclusively enriched with or made up of the three essential branched chain aminoacids, as it appears e.g. from the already mentioned British Pat. No. 2037161 and from the Italian Patent Application No. 29414 A/78 filed on Nov. 3, 1978 in the name of the same applicant. The administration of these aminoacids produces positive therapeutical effects, which support the hypothesis of a remarkable anticatabolic and anabolic effect of such aminoacids. On the other hand it is proved that the contribution of the three essential branched aminoacids exerts an anabolic effect, especially evident at the level of muscular proteins. During an intense physical cise, in which a reduction in the proteinic synthesis and an increase of the proteinic degradation in the muscular tissue and in the whole organism occur, an increased oxidation of aminoacids, and particularly of branched chain aminoacids at muscular level seems to be ascertained.

Beside the exogenous contribution of essential aminoacids by infusional route, the administration of aminoacids orally, where it is consistent with the pathological state, has been spreading to a certain extent, but with scarcerly encouraging results. As it is well understandable, this route of administration, owing to its characteristics of practicalness, could be the preferential one in all the occasions which do not involve emergency situations or the impossibility of taking liquids.

The principal hindrance to the diffusion of the oral route of administration is represented by the scarce desirability of these aminoacid mixtures, particularly, in the presence of methionine, tryptophan and tyrosine, owing to the bad organoleptic characteristics of these aminoacids, or, in the presence of leucine and isoleucine, owing to the persistent bitter taste. Administration in these conditions involves with a high frequency (from 35% to 70% of the cases) the regurgitation of what has been taken. Often used expedients in order to modify the organoleptic characteristics of these mixtures, sometimes nauseating and disgusting, are the addition of considerable quantities of flavouring substances, as fruit, vanilla, cocoa, coffee flavours, etc., the mixing with carbohydrates such as glucose, fructose, saccharose and other mono- and disaccharides, polyalcohols such as sorbitol, mannitol and ylitol and excipients such as maltodextrins, in quantities varying from 1% to 10%. In spite of these types of natural or synthetic correctives introduced into the daily practice, phenomena of gastric intolerance are often registered (particularly after administration of mixtures containing methionine and tryptophan). The phenomena of regurgitation following the administration by oral route of the mixtures containing such aminoacids prevent from continuing the therapy with such types of oral formulations, which should be on the other hand particularly favourable in case of both elderly and of tender age patients, where the oral administration may be an attracting alternative to the infusional route.

On the other hand, even if the patient does not feel repugnance against the common oral formulations above mentioned, their administration can be awkward or even dangerous in some pathological situations. In fact the high amounts of carbohydrates, which are normally contained therein, do not fit, owing to the high caloric contribution of the glucidic component, to the therapy of patients with weight, cardiovascular or atherosclerotic troubles, while they are certainly dangerous in the treatment of diabetic patients. In any case, it is suitable to avoid an abnormal contribution of additives and carbohydrates also in other cases of dismetabolism where the exogenous administration of amino acids is necessary. On the other hand it should be pointed out that the prolonged use of flavoured formulations, in order to try to mask the disgusting organoleptic characteristics, likewise causes a sense of repulsion on the long run. If, on the contrary, it is tried to reduce the number and amount of excipients and flavouring substances, the bitter taste of the aminoacids, on the one hand, and the high incidence of nausea and vomiting, on the other hand, make such formulations so scarcerly desirable that they are doomed to be sooner or later refused by the patient. The situation does not improve when tablet formulations are examined. In fact, also in this case the bitter taste and the disgusting organoleptic characteristics cannot be masked by flavouring substances or by coating the tablets by means, e.g., of chocolate, unless it is accepted to scatter the amino acids into so large a mass of diluents that the latter are to be considered as the main constituents of the tablet. In this case it is evident that to get the therapeutically effective daily dose of amino acids it has to be administered a so large number of tablets that their taking is made difficult and this artifice devoid of any practical usefulness. See in this regard U.S. Pat. No. 3764703, wherein there is described the preparation of tablets, which includes a preliminary dispersion of amino acid mixtures into a certain amount of polyvinylpyrrolidone as the binding agent, a subsequent drying and sifting, a dilution of the obtained powder with starch and calcium stearate and a final compression. The single tablets, the disaggregability of which is evaluated according to the regulations of the British Pharmacopoeia, are then coated by a protective film of polyvinylacetate and polyethylene glycol in order to assure the masking of bitter taste. Tablets of acceptable weight and size are so obtained, so that administration of about 30 tablets allows to get a therapeutically useful daily maintenance dose. It is in fact to be noted that such tablets are planned to integrate the infusional basic therapy. Even though nothing has been reported about possible side effects concerning nausea and vomiting, it is clear that administration of such tablets is a remarkable trouble to the patient, as he should continually take more than a tablet every hour within the span of 24 hours or, considering the rest time, more than two tablets per hour.

Therefore, it can be concluded that administration by oral route of the at present available formulations appears to be scantily applicable.

SUMMARY OF THE INVENTION

This invention intends to eliminate all the limitations concerning the current formulations of L-α-amino acid mixtures for oral administration. In fact, it has been found that homogenous mixtures of components having extremely labile nature, such as L-α-amino acid mixtures, either in the form of powder or paste, i.e. with a moisture degree between 1 and 50% by weight the dry mass, lend themselves, under particular operative conditions, to be subjected to an extrusion process, without any alteration of the chemical nature and pharmacological properties of the single components.

In fact, the extrusion process allows the production of granules or pellets of regular shape, the size of which can be changed at will, characterized by a reduced porosity and a high density. These particular characteristics of the granule allow each component of the mixture forming the granule to be released in a gradual and controlled way. As a further consequence of the high relative density and, hence, the reduced superficial area, the compact granule according to this invention assures, also without having resort to a possible coating process, a good degree of desirability, the minimization of the bitter aftertaste and the masking of any unpleasant smell. On the other hand, as granules, owing to their compactness, lend themselves to a coating process. The coating of the granule with a protective film, beside ameliorating the organoleptic characteristics of the pharmaceutical or dietetic form, enhances the delayed disaggregation characteristics of the granule in the chosen portion of gastroenteric tract.

Hence the formulations obtained in accordance with the present invention are particularly useful because they hide unpleasant tastes and smells, and enable the granule to be gradually released in the chosen portion of gastro-intestinal tract, thus avoiding all phenomena of intolerance and regurgitation due to amino acids. The main purpose of this invention is, therefore, to realize pellets having regular and predeterminable geometric shape and size changeable at will, characterized by a reduced porosity and by a high relative density. The pellets according to this invention may contain mixtures of natural or synthetic substances, pharmacologically or physiologically active and labile, as e.g. mixtures of α-amino acids, vitamins, etc. so as to get a controlled gradual release of active components both in the presence and the absence of the protective film. When, for instance, the release of components such as the amino acids is wanted to occur at pancreatic level, the granules can be coated by a protective film realized by depositing a thin layer of a vegetable protein, e.g. zein extracted from maize. Such a protein, having a molecular weight of about 38,000 daltons, characterized by the presence of a large number of lateral acidic chains, is practically insoluble in water, while it is soluble in hydroalcoholic solutions, which allows a uniform deposit of it on granules, which, once dried, turn out to be practically waterproof. The subsequent complete digestibility by the pancreatic enzymes allows dissolution of zein and disaggregation of the granule together with consequent release of amino acids. Instead of zein other proteins, such as chotylin and keratin, may be used. The protection of granules by means of such proteins which are toxicologically inert and in turn biodegradable into amino acids is to be preferred and particularly useful in all the preparations of amino acid mixtures to be administered by oral route in the presence of serious metabolic damages such as nephro- and hepatopathy and particularly in the therapy of cirrhotic forms. If particularly long-lasting disaggregation times are preferred, the coating of granules may be realized by means of natural resins, such as gum arabic, while in all the cases where a particularly strong gastroresistance is wanted, the coating of granules may be realized by means of synthetic polymers such as cellulose polymethylmethacrylate and acetophthalate. If, on the contrary, the release of the active agents at gastric level is considered suitable, the pellets can be coated by a thin layer of a sugar, such as saccharose or glucose, or else a polyalcohol, such as xylitol or mannitol.

All these types of coating, although not strictly necessary, also help the swallowing process, thanks to their smooth and/or sweetened surface.

As above mentioned, the granules may have different size, but, in any case, as a rule, they are smaller than the current tablets or pastilles. They are preferably realized in the form of little cylinders with a diameter ranging from 0.5 mm to about 8 mm and preferbly of about 2 mm. The height of the small cylinder ranges at will from 1 to several mm, but preferably is of about 2 mm.

The cylindrical granules are obtained by extrusion of an α-amino acid mixture in the form of powder or paste with water through a die, the screw of which exerts on the mass to be extruded a pressure ranging from 5 to 200 kg/cm$^2$. At the exit from the die a rotary knife placed at a suitabledistance cuts the extruded compacted material. The rotation speed and the distance of the cutting knife from the holes of the die are adjusted in such a way as to obtain small cylinders of uniform length, which can be modified at will and uniformly by varying the said distance and rotation speed. The same result can be obtained, of course, by extrusion through a die moving with respect to a fixed cutting knife. Also in this case the length of the extruded little cylinders depends on the rotation speed of the die and on the distance of the cutting knife. If the extrusion has been carried out on a moistened paste, the little cylinders are the submitted to drying into an air oven and/or fluid-bed desiccators for a time and at a temperature, which vary in accordance with the moisture degree and composition of the granulate, providing a solid and compact stuff, completely identical to the one obtained by extrusion of powder.

The so obtained cylindrical pellets can at this point be submitted to the coating process, carried out, for instance, by wetting them into a rotary pan at a speed ranging from 5 to 50 r.p.m. with a solution of the coating substance into a suitable solvent. The solvent, in the case of coatig materials of proteinic nature, such as zein, keratin and chotylin, can be water or a lower alcohol such as ethanol, propanol and isopropanol or their mixtures. After passing in the coating pan, the solvent is evaporated by means of air jet at a temperature ranging between room temperature and 80° C. The coating of pellets can also be obtained by spraying the solution, alternated with an air insufflation, and this allows to obtain a homogeneous coating of the single small cylinders and a fast removal of the solvent as well.

In coating by means of proteins extracted from maize gluten, hydroalcoholic solutions of these proteins (zein) at variable concentrations ranging between 5 and 40% w/v are used. In order to obtain a good compromise between sprinkling time, solvent evaporation time and mean thickness of the coating substances ranging between few microns and many hundredths of millimeter, the fittest concentrations are included between 10 and 20% w/v, the preferred concentration being equal to 15% w/v. The diluent is normally made of water-ethanol mixtures in ratios ranging between 30:70 and 10:90. If the coating substance used is a polyacrylate such as polymethylmethacrylate, the resin is dissolved in a concentration from 1 to 25% in acetone or isopropanol and related mixtures. If the coating substance used is a cellulose derivative such as cellulose phtalate or acetophthalate, it is used in concentrations between 1 and 10% in acetone and chloroform.

As already mentioned, the powder or paste subjected to extrusion is made of homogeneous mixtures of essential and non-essential L-α-amino acids, alone or also mixed with binding agents, adjuvants and excipients. The binding agents chosen in the group formed by starches, cellulose and their derivatives, such as methylcellulose, hydroxypropylmethylcellulose, hydroxypropylcellulose etc., can be added to the paste in a proportion of 0.1–30% by weight of the mass of amino acids, while the adjuvants and inert excipients, such as cellulose, starch, maltodextrine and lactose, are possibly used for diluting the active agents in a ratio varying from 0.1 to 4 times the mass of amino acids. If it is preferred to moisten the mixture to be extruded in order to make easier the extrusion process, the maximum degree of humidity of the paste to be extruded is equal to 50% in comparison with dry weight, but also humidity values of 1%, corresponding to the dry powder, are perfectly consistent with the extrusion process. As already mentioned, moisturizing is completely optional, as the humidity itself of raw materials and/or crystallization water of the substances forming the mixture allow to obtain the compaction of ingredients. If during the extrusion the temperature tends to increase too much, e.g. above 80° C., the die can be cooled so that the operating conditions do not modify, in any case, the characteristics of the extruded product.

When the mixture of amino acids is inteded for a merely dietetic use, such as, e.g., a diet integrator for athletes or for overalimentation, it can be integrated with additives, such as sugars like fructose, saccharose, glucose; proteins like powdered skimmed-milk, lactalbumin, casein, soya proteins and serum albumin; Na, Ca, K, Mg, P, Cl, etc. mineral salts; oligoelements like Fe, Zn, Cu, Mn, Co; vitamins like vitamins of the B complex, vitamin C, A, D$_2$, PP; and other active agents like carnitine and panthetine.

The granular formulation obtained by extrusion according to the present invention and made up of granules of qualitatively and quantitatively variable composition, possibly coated with an almost water-insoluble film which, however, can be attacked by gastric and pancreatic enzymes, allows oral administration of any amino-acid mixture. The small cylindrical granules are particularly suitable for an easy and fast swallowing of a solid, practically odourless and tasteless or slightly flavoured mass, the density and consistency of which allow a relatively slow disaggregation by gastroenteric juices thus avoiding undesirable accumulations of amino acids, responsible for the gastric-intolerance phenomena. The reduced size of the small compact and dense cylinders overcomes the inconvenience of ingesting large tablets, and at the same time the compactness and the reduced porosity of granules do not enable, even in the absence of a coating, the same pellets to be considerably dissolved during the short stay in the oral cavity on deglution.

The granular shape according to this invention, besides eliminating the scanty desirability and the first causes of reduced gastric tolerance phenomena, which are met by administration of amino acid solutions and-/or granulates available at present, enables to avoid the carrying of said granulates with an excess of aromatizing substances and/or carbohydrates, the use of which is inappropriate in dismetabolic pathologies and particularly in those of diabetic nature.

Pellets obtained by the process according to the invention are of general applicability and are suitable for any type of pharmaceutical or dietetic preparation including mixtures of natural L-α-amino acids and their recemates as well as mixtures of such amino acids with other substances of glucidic or proteinic nature, vitamins, mineral salts, oligoelements and therapeutically and dietetically active agents. By the present preparation process the organoleptic characteristics of solid amino acid mixtures are so improved that pellets can also be employed outside the therapeutic prescriptions and coercions as integrators of the normal alimentation, such as in case of unbalanced diets, intense bodily exercise, hyperalimentation, etc.

In order to facilitate the highest degree the swallowing and ingestion of the granular preparations according to the present invention the pellets have a preferably cylindric shape with a diameter ranging between 0.5 and some millimeters and a length equal to about 1–4 times the diameter.

Although till now reference was mainly made to cylindrical granules, it is obvious that by the process according to the present invention pellets of a different shape can be obtained, such as cubic, prismatic, egg-shaped pellets, and/or granules having a star- or ring-shaped, transversal section etc. as it is well known to those skilled in the field of alimentary and dietetic pasta or of gunpowder granules. Anyway, it is convenient that in any case the shape is as compact as possible and the ratios between the three largest reciprocally orthogonal dimensions are as close to 1 as possible.

As previously mentioned, the swallowing of pellets suspended in a suitable beverage at a temperature preferably equal to or lower than room temperature is made easier if the single pellets are coated with a thin layer of a physiologically acceptable macromolecular film-forming substance chose in the group including proteins, carbohydrates, natural resins and rubbers as well as synthetic polymers. This coating can be obtained by immersion in or spraying of a solution of such film-forming substances, possibly repeated and alternated with evaporation of the solvent.

An example of oral composition for nephrology, where weight ratios between the single amino acids are particularly suitable for the treatment of any state of acute and chronic renal insufficiency, involves the following weight ratios between leucine, phenylalanine, lysine hydrochloride, methionine, valine, isoleucine, threonine, histidine, tryptophan and tyrosine, respectively: 1.0:0.34:0.82:0.85:1.43:1.0:1.26:0.61:0.18:0.21. An example of gastroprotected granular formulation for the treatment of chronic hepatopaties has the following mean composition: L-valine 23 parts, L-leucine 23 parts, L-isoleucine 11.5 parts, maize starch 9.5 parts, saccharose 5.8 parts, methylcellulose 1 part. Gastroprotected small cylinders having this percent composition are utilized, for instance, for preparing unit-dose packets weighing 6.4 g and containing 5 g of branched chain amino acids. The mean daily dose for adults can vary from 2 to 8–10 packets, while in the case of cirrhotic patients the dose is prudently limited to a maximum of 4 packets a day, equal to 20 g pro die of branched amino acids.

Thanks to the anabolic effect of the triad of branched chain amino acids, the association of such amino acids with milk proteins and glucose and fructose allows a rapid recovery of energy and reduces the metabolic stress of persons submitted to physical efforts. The gastroprotected granular formulation is particularly suitable to this purpose being easily transportable when wrapped in packets, ready for use and of easy ingestion. Also in these cases the formulation according to this invention is based on the use of the triad of branched chain amino acids as a dietetic integrator and the optimal dose of the amino acids mass ranges from 0.3 to 0.5 g per kg of body weight pro die.

The addition of carbohydrates contributes to make the diet hypercaloric as it is suitable to sportsmen. The optional flavouring with several tastes like orange, lemon, cocoa can increase the desirability of granulate.

The granular products according to this invention can be wrapped in packets weighing from about 30 to 40 g according to the following formulations:
  valine—g 2.00,
  leucine—g 2.00,
  isoleucine—g 1.00,
  glucose—g 10.00,
  fructose—g 10.00,
  75% lactalbumin—g 4.00,
  citric acid—g 0.60,
  WE 15 Sucrester (surfactant)—g 0.20,
  orange flavour—g 0.20.

Another formulation with the same amounts of the same amino acids provides for the substitution of lactalbumin with 10 g of powdered skimmed milk, of citric acid with 2.5 g of cocoa, of WE 15 Sucrester with Labrafil and of orange flavour with cocoa flavour. (Sucrester and Labrafil are registered trademarks).

The present invention will be now explained on the basis of some specific embodying examples, which, however, are not to be considered as limiting, and where the parts are parts by weight.

EXAMPLE 1

A mixture formed by the relevant parts by weight of following amino acids:
  L-Leucine—1000,
  L-phenylalanine—430,
  L-lysine hydrochloride—1140,
  L-methionine—970,
  L-valine—1280,
  L-isoleucine—1000,
  L-threonine—1140,
  L-histidine—710,
  L-tryptophan—280,
  L-tyrosine—300,
is put in a mechanical mixer with interpenetrating arms and 1350 parts of maize starch are added to it. The powders are homogenized in the mixer for 15 minutes and the obtained mixture made up of L-amino acids and maize starch is dampened with 140 parts of methylcellulose dissolved in 2400 parts of purified water. During dampening the powders contained in the mixer are kept in motion by the interpenetrating arms and the complete dampening operation is performed in about 10 minutes.

The damp mass is put in the charging hopper of a dice-making machine and is pushed toward the perforated die (diameter of the holes 2 mm) by means of a screw feeder which compresses the mass at 70 kg/cm$^2$. The extruded product is cut in the shape of small cylinders having a length of 2 mm by means of a knife rotating at a speed of 500 r.p.m. The small cylinders are collected on trellis and let dry for 3 hours into a forced-air oven thermostated at 60° C.

The dried small cylinders are put into a rotary pan (20 r.p.m.) and coated with 250 parts zein dissolved in an ethanol-water mixture 9:1 (1000 parts). The coating with zein solution is carried out by successive additions of little portions (80 parts) by drying with hot air at 45° C. after each addition.

The small cylinders are then coated, always into a rotary pan, with 580 parts xylitol dissolved in 1450 parts of purified water.

One gram of the so obtained granular product is put into a tube of the equipment for measuring the disaggregation time of tablets and capsules according to Official Pharmacopoeia of the Republic of Italy, eighth edition, page 451. The tube is alternatively raised and lowered by a mechanical arm into a vessel containing distilled water at 37° C. until granules are disgregated. The required time is about 30 minutes.

EXAMPLE 2

A mixture made up of 2000 parts leucine, 2000 parts valineand 1000 parts isoleucine is put into a mechanical mixer with interpenetrating arms, and 800 parts maize starch and 80 parts methylcellulose are added to it. The powders are homogenized for 15 minutes. The obtained mixture is put into the charging hopper of a dice-making machine and fed to a perforated rotary die (diameter of the holes 2 mm). The revolving speed of the die is of about 5 r.p.m.. The extrusion occurs through an eccentric pressure roller. Compact small cylinders are discharged from the rotary die, which are cut by a fixed blade positioned at a distance of 2 mm from the rotary die.

The small cylinders are put into a rotary pan (20 r.p.m.) and coated with 500 parts saccharose dissolved in 1200 parts of purified water. The coating technique is similar to that described in Example 1.

EXAMPLE 3

Starting from a mixture having the following composition in parts by weight:
L-leucine—2000,
L-valine—2000,
L-isoleucine—1000,
maize starch—800,
methylcellulose—80,
and acting according to the process described in Example 2, pellets are obtained, the coating of which is effected according to the process of Example 1, with the difference that instead of zein 200 parts polymethylmethacrylate dissolved in 2000 parts of an acetone-isopropanol mixture 6:4 and instead of xylitol 500 parts saccharose are used.

EXAMPLE 4

According to the preparation process described in Example 2, pellets are prepared starting from a mixture having the following composition in weight parts:
L-leucine—2000,
L-valine—2000,
L-isoleucine—1000,
maize starch—800,
methylcellulose—80.

The obtained pellets are coated according to the process described in Example 1, with the difference that 600 parts zein in hydroalcoholic solution and 1300 parts saccharose in aqueous solution are used.

EXAMPLE 5

Acting in accordance with the process described in Example 1, pellets are prepared starting from a mixture having the following composition in weight parts:
L-leucine—1000,
L-phenylalanine—430,
L-lysine hydrochloride—1140,
L-methionine—970,
L-valine—1280,
L-isoleucine—1000,
L-threonine—1140,
L-histidine—710,
L-tryptophan—280,
L-tyrosine—300,
maize starch—1350,
methylcellulose—140.

Pellets are coated according to the process of Example 1, with the difference that 200 parts polymethylmethacrylate dissolved in 2000 parts of an acetone-isopropanol mixture 6:4 and 580 parts saccharose in aqueous solution are used.

EXAMPLE 6

Acting in accordance with the process described in Example 2, pellets are prepared starting from a mixture having the following composition in weight parts:
L-valine—1000,
L-leucine—1000,
L-isoleucine—500,
L-carnitine—500,
glucose—5000,
fructose—5000,
skim milk—5000,
Sucrester (surfactant)—100,
cocoa—1250.

The obtained pellets are packaged without any coating.

EXAMPLE 7

According to the process described in Example 2, pellets are prepared starting from a mixture having the following composition in weight parts:
L-valine—1000,
L-leucine—1000,
L-isoleucine—500,
glucose—5000,
fructose—5000,
lactalbumin—2000,
Sucrester (surfactant)—100,
citric acid—300,
orange flavour—100.

Also in this case the pellets are not coated.

EXAMPLE 8

Following the method described in Example 2 pellets are prepared starting from a mass having the following composition:
L-valine—kg 2,
L-leucine—kg 2,
L-isoleucine—kg 1,
glucose—kg 10,
fructose—kg 10,
lactalbumin—kg 4,
Sucrester—kg 0.2,
citric acid—kg 0.6,
lemon flavour—kg 0.4,
vitamin A I.U.—1,788,000,
vitamin D2 I.U.—164,000,
vitamin E I.U.—12,000,
vitamin B6—g 0.75,
vitamin B2—g 0.36,
vitamin B1—g 0.55,
vitamin PP—g 10,
vitamin C—g 23,
vitamin B12—mg 1.75,
folic acid—mg 154,
calcium pantothenate—g 3.6,
calcium gluconate—g 110,
calcium phosphate—g 620,
iron glycerophosphate—g 40,
magnesium sulphate—g 1.8,
zinc chloride—g 11.3,
potassium iodide—g 0.79, potassium chloride—g 192,
potassium glycerophosphate—g 509,
manganese chloride—g 210,
copper sulphate—g 1.9.

Even in this case the pellets are not coated.

From density measurements carried out on all the granular products obtained by the process of this invention on the basis of given examples, the apparent density of the new granular products is comprised between 0.4 and 0.7, i.e. definitely greater than that of the common pharmaceutical granulates. The apparent density of extruded pellets, when coated or not coated, has been measured by freely pouring into a graduated cylinder the extruded small cylinders, without any motion aiming at increasing their compaction degree, such as vibrations, compressions, etc. The values obtained by the formula:

$$\text{apparent density} = \frac{\text{Weight of unit volume of granulate}}{\text{Weight of unit volume of one pellet}}$$

turned out to be, on average, 0.6 g/ml, which is a definitely high value, considering the particularly low apparent density of raw materials used in manufacturing (e.g. the apparent density of amino acids is about 0.3 g/ml).

Although this invention has been described on the basis of some at present preferred embodiments, it is obvious that variations and/or changes can be made by those skilled in the art without departing from the spirit and scope of the invention.

For instance, other extrusion and cutting methods could be used, when also applied to pharmaceutical or alimentary products for human or animal use which are suitable for preparing granular formulations.

What is claimed is:

1. Dietetic pellets comprising a beneficial core consisting essentially of a therapeutically effective amount of a compacted mixture of the free amino acids leucine, valine and isoleucine in a weight ratio of 2:2:1 in admixture with about 0.1–30% of a pharmaceutically acceptable binding agents based on the weight of said amino acid mixture, and a pharmaceutically acceptable adjuvant or diluent in an amount of about from 0.1 to 4 times the mass of said amino acid mixture, said pellets having an apparent density of between about 0.4 and 0.7 g/ml.

2. Dietetic pellets according to claim 1 wherein said binding agent, adjuvant, and diluent are selected from the group consisting of proteins, sugars, vitamins, mineral salts and flavoring agents.

3. Dietetic pellets according to claim 1 wherein said core has the following composition in parts by weight: leucine 2000, valine 2000, isoleucine 1000, maize starch 800, methylcellulose 80.

4. Dietetic pellets according to claim 1 wherein said core has the following composition in parts by weight: leucine 1000, valine 1000, isoleucine 500, glucose 5000, fructose 5000, lactalbumin 2000, surfactant 100, citric acid 300, orange flavor 100.

5. Dietetic pellets according to claim 1, wherein said core is surrounded by a water-resistant protective coating soluble in gastroenteric juices and consisting essentially of zein or a mixture of zein with carbohydrates.

6. Dietetic pellets according to claim 3, wherein said core is coated with zein and saccharose.

7. Dietetic pellets according to claim 1, wherein said binding agent is a mixture of starch and methylcellulose.

8. A method of administering amino acids to a person, comprising the step of orally administering dietetic pellets comprising a beneficial core consisting essentially of a therapeutically effective amount of a compact mixture of the free amino acids leucine, valine and isoleucine, in a weight ratio of 2:2:1, in admixture with about 0.1-30% of a pharmaceutically acceptable binding agent based on the weight of said amino acid mixture, and a pharmaceutically acceptable adjuvant or diluent in an amount of about from 0.1 to 4 times the mass of said amino acid mixture, said pellets having an apparent density of between about 0.4 and 0.7 g/ml.

9. A method according to claim 8 wherein said binding agent, adjuvant, and diluent are selected from the group consisting of proteins, sugars, vitamins, mineral salts and flavoring agents.

10. A method according to claim 8 wherein said core has the following composition in parts by weight: leucine 2000, valine 2000, isoleucine 1000, maize starch 800, methylcellulose 80.

11. A method according to claim 8, wherein said core has the following composition in parts by weight: leucine 1000, valine 1000, isoleucine 500, glucose 5000, fructose 5000 lactalbumin 2000, surfactant 100, citric acid 300, orange flavor 100.

12. A method according to claim 8, wherein said core is surrounded by a water-resistant protective coating soluble in gastroenteric juices and consisting essentially of zein or a mixture of zein with carbohydrates.

13. A method according to claim 10, wherein said core is coated with zein and saccharose.

14. A method according to claim 8, wherein said binding agent is a mixture of starch and methylcellulose.

* * * * *

UNITED STATES PATENT AND TRADEMARK OFFICE
CERTIFICATE OF CORRECTION

PATENT NO. : 4,753,804
DATED       : June 28, 1988
INVENTOR(S) : IACCHERI et al

It is certified that error appears in the above—identified patent and that said Letters Patent is hereby corrected as shown below:

Title page:

[73] Assignee: BOEHRINGER BIOCHEMIA ROBIN S.p.A.
Milano, Italy

Signed and Sealed this

Thirteenth Day of December, 1988

Attest:

DONALD J. QUIGG

Attesting Officer

Commissioner of Patents and Trademarks